(12) United States Patent
Lin

(10) Patent No.: US 6,786,903 B2
(45) Date of Patent: Sep. 7, 2004

(54) ROTARY DEVICE FOR FIXING SPINAL COLUMN UNDER TREATMENT

(75) Inventor: Chih-I Lin, Chino Hills, CA (US)

(73) Assignee: A-Spine Holding Group Corp., Tortola (VG)

( * ) Notice: Subject to any disclaimer, the term of this patent is extended or adjusted under 35 U.S.C. 154(b) by 181 days.

(21) Appl. No.: 10/107,401

(22) Filed: Mar. 28, 2002

(65) Prior Publication Data

US 2003/0187434 A1 Oct. 2, 2003

(51) Int. Cl.⁷ .............................................. A61B 17/56
(52) U.S. Cl. ......................................... 606/23; 606/61
(58) Field of Search .............................. 606/61, 72, 73

(56) References Cited

U.S. PATENT DOCUMENTS

| | | | | |
|---|---|---|---|---|
| 5,562,663 A | * | 10/1996 | Wisnewski et al. | 606/61 |
| 6,077,262 A | * | 6/2000 | Schlapfer et al. | 606/61 |
| 6,110,172 A | * | 8/2000 | Jackson | 606/61 |
| 6,139,549 A | * | 10/2000 | Keller | 606/61 |
| 6,251,112 B1 | * | 6/2001 | Jackson | 606/61 |
| 6,440,132 B1 | * | 8/2002 | Jackson | 606/61 |
| 6,458,132 B2 | * | 10/2002 | Choi | 606/61 |
| 6,565,565 B1 | * | 5/2003 | Yuan et al. | 606/61 |
| 6,652,526 B1 | * | 11/2003 | Arafiles | 606/61 |
| 2002/0116001 A1 | * | 8/2002 | Schafer et al. | 606/61 |
| 2002/0120272 A1 | * | 8/2002 | Yuan et al. | 606/61 |
| 2003/0100904 A1 | * | 5/2003 | Biedermann | 606/73 |
| 2003/0125742 A1 | * | 7/2003 | Yuan et al. | 606/61 |

* cited by examiner

*Primary Examiner*—Pedro Philogene
*Assistant Examiner*—D. Austin Bonderer
(74) *Attorney, Agent, or Firm*—Bacon & Thomas, PLLC

(57) ABSTRACT

A vertebral fixation device. The device includes a fixation seat, a fixation block, and a fastening bolt. The fixation seat is provided with a receiving slot for receiving a vertebral fixation rod. The fixation block is engaged with the fixation seat such that the vertebral fixation rod is pressed by the fixation block, and two retaining edges of the fixation block are retained in two retaining recesses of the fixation seat. The fastening bolt is engaged with a threaded through hole of the fixation block such that one end of the fastening bolt presses against the vertebral fixation rod.

11 Claims, 10 Drawing Sheets

US 6,786,903 B2

ROTARY DEVICE FOR FIXING SPINAL COLUMN UNDER TREATMENT

FIELD OF THE INVENTION

The present invention relates generally to a spinal surgical care device, and more particularly to a rotary device for fixing spine column under treatment.

BACKGROUND OF THE INVENTION

The conventional backbone-fixing devices comprise a backbone fixing rod which is held securely by a fastening bolt and a nut. However, the conventional devices are not provided with means to locate temporarily the fixing rod in the surgical operation. For this reason, the fixing rod is susceptible to unintentional displacement in a spinal surgery in progress. Such a displacement of the back-fixing rod often affects adversely the outcome of the spinal surgery. In addition, the conventional backbone-fixing devices must be used in conjunction with one or more special hand tools, thereby complicating the spinal surgery. In order to overcome deficiencies of the prior art devices described above, this inventor of the present invention disclosed the vertebral fixation devices in the U.S. Pat. Nos. 5,387,212 and 5,582,612. These two devices call for further improvements.

SUMMARY OF THE INVENTION

The primary objective of the present invention is to provide a rotary device for fixing spinal column under treatment. The rotary device comprises a fixation seat, a fixation block, and a fastening bolt. The fixation block is provided with means to hold temporarily a fixation rod in the course of a surgical operation, thereby minimizing the risk that the fixation rod is displaced. In addition, the fixation seat is provided with means to cooperate with a spherical head device.

The fixation device of the present invention comprises a fixation seat, a fixation block, and a fastening bolt. The fixation seat is provided with a receiving slot which is provided on two opposite inner walls with a retaining recess. The fixation block is provided with a rotary control end, a threaded through hole, and two retaining edges. The retaining edges of the fixation block are retained in the retaining recesses of the fixation seat. The fastening bolt is engaged with the threaded through hole of the fixation block.

The fixation block is provided in the underside with an arcuate surface which is provided with a plurality of protruded edges. The arcuate surface and the protruded edges serve to hold securely a fixation rod.

The retaining recesses of the fixation seat may be located on the inner walls or outer walls of the receiving slot of the fixation seat. The retaining edges of the fixation block may be located on the outer edges or inner edges of the fixation block, so as to cooperate with the retaining recesses of the fixation seat.

The retaining edges of the fixation block are of a slanted construction, thereby enabling the fixation block to have a pressing effect on the fixation rod at the time when the retaining edges are retained in the retaining recesses of the fixation seat.

The bottom edge of the rotary control end of the fixation block is an inclined plane which has a higher inner side and a lower outer side. The top edge of two side walls of the fixation seat is an inclined plane with a lower outer side and a higher inner side. The two inclined planes may push against each other.

The outer surface of the two side walls of the fixation seat is provided with a clamping slot adapted to be held by a hand tool.

The fixation seat may be provided with a screw which is made integrally therewith and is any kind of screw in existence.

The fixation seat may be provided with a hooked body which is made integrally therewith and is any kind of hooked body in existence.

Preferably, said fixation seat is provided in the bottom with a through hole, and is further provided with a fixation apparatus comprises a spherical head and a press ring, wherein said spherical head and said press ring are adapted to be received in said through hole with said press ring resting on said spherical head, and said spherical head and said press ring will be pressed securely in the fixation seat by a fixation rod, when the fixation block is joined with said fixation seat. More preferably, said fixation seat is further provided with an assembly ring, wherein said assembly ring which is adapted to mounted to said through hole so that said spherical head is clamped between said assembly ring and said press ring. Preferably, said spherical head is provided with a fastening screw made integrally therewith for fastening onto a bone or spinal segment, wherein said fastening screw is extruding from said through hole when said spherical head is received in said through hole.

The top, bottom, top surface, bottom surface, top edge, bottom edge, etc., are used in this specification in relation to an upright human body. The inner, outer, inner side surface, outer side surface, etc., are used in this specification in relation to the component part referred to.

The features and the advantages of the present invention will be more readily understood upon a thoughtful deliberation of the following detailed description of the present invention with reference to the accompanying drawings.

DETAILED DESCRIPTION OF THE PREFERRED EMBODIMENTS

Figure 1:
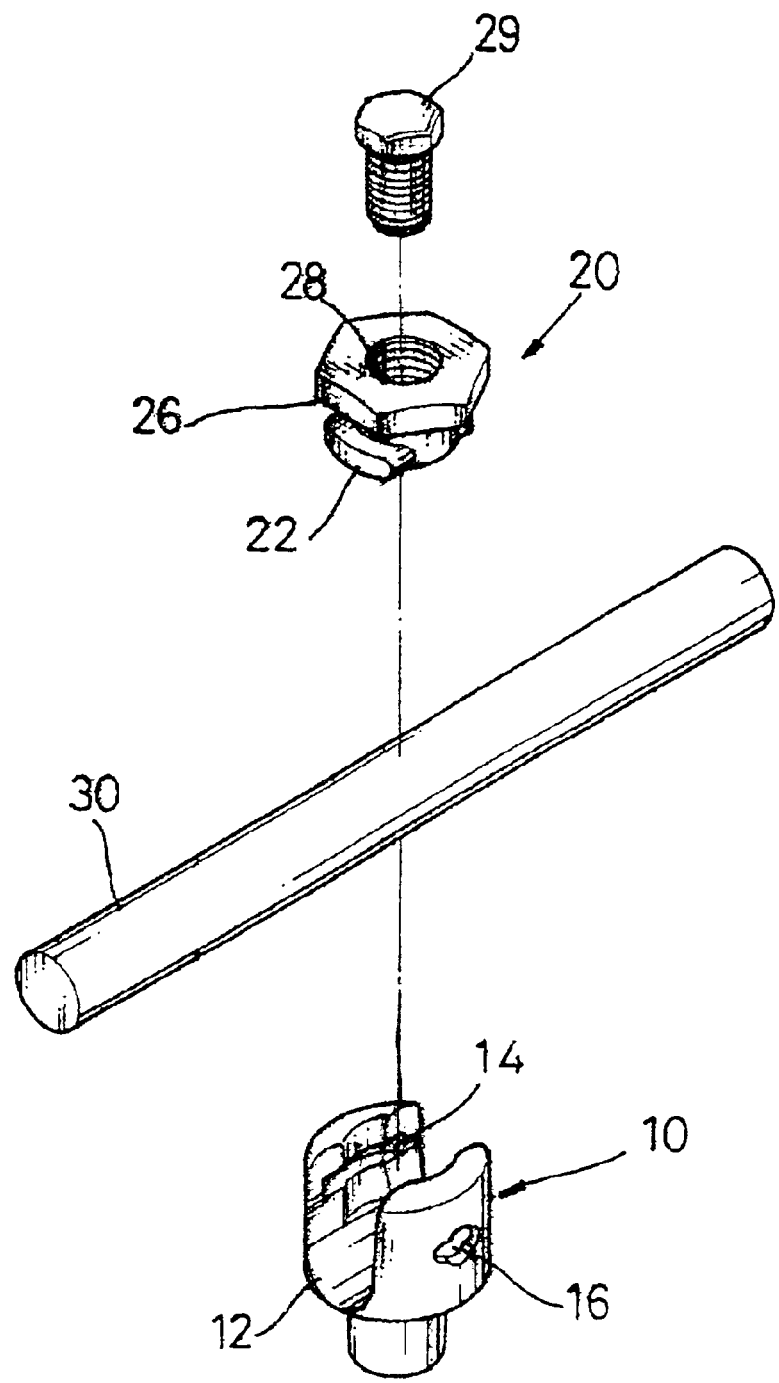
FIG. 1 shows an exploded view of a first preferred embodiment of the present invention.
Figure 2:
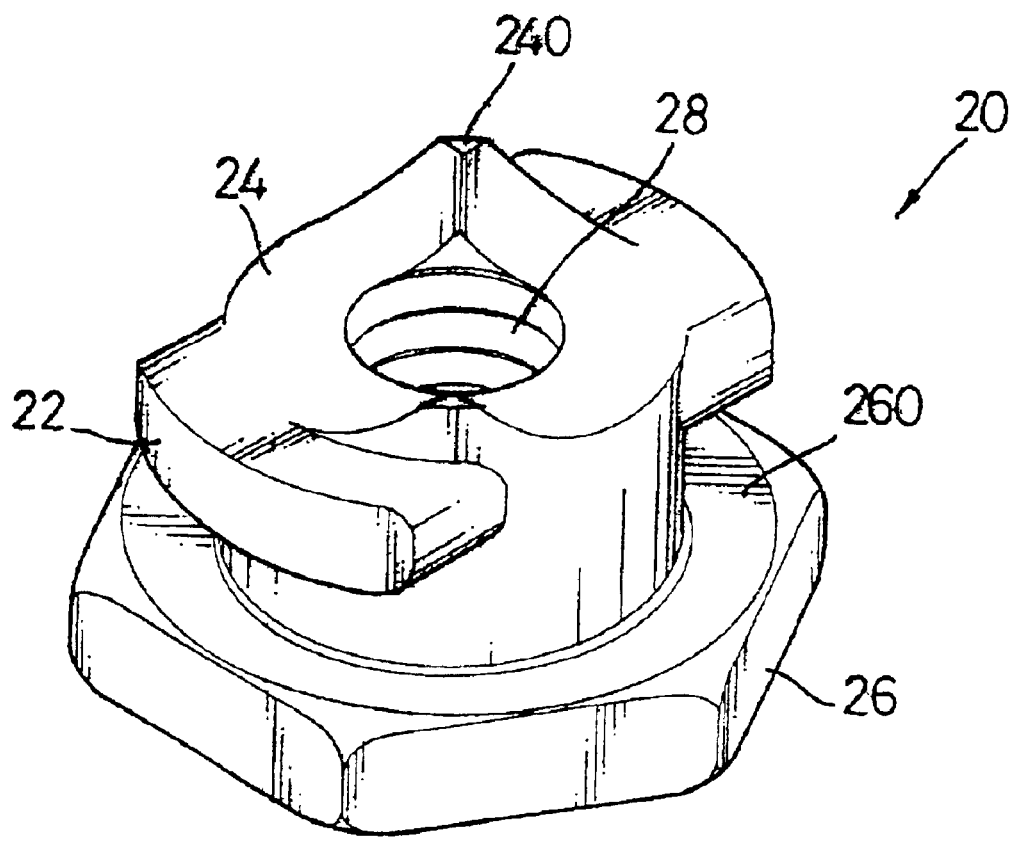
FIG. 2 shows a schematic view of the fixation block of the present invention.
Figure 3:
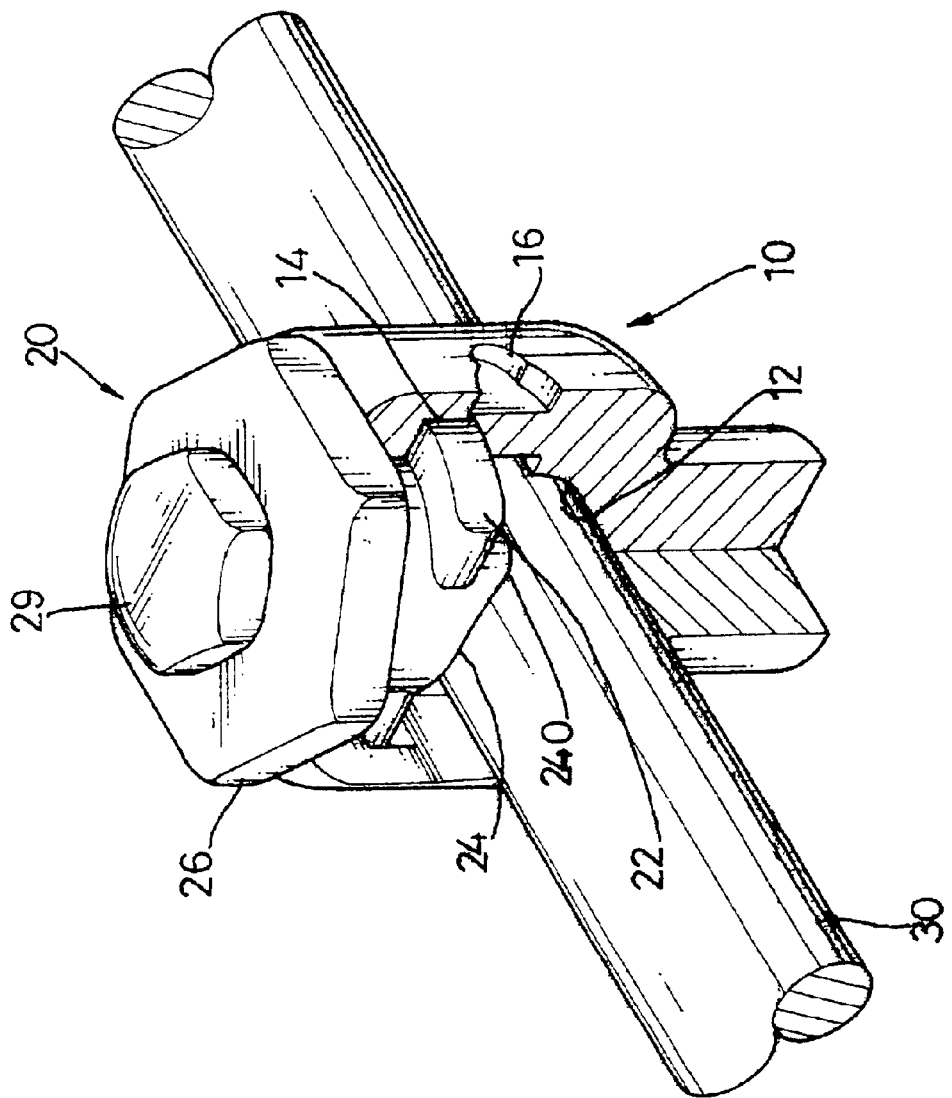
FIG. 3 shows a schematic view of the present invention at work.
Figure 4:
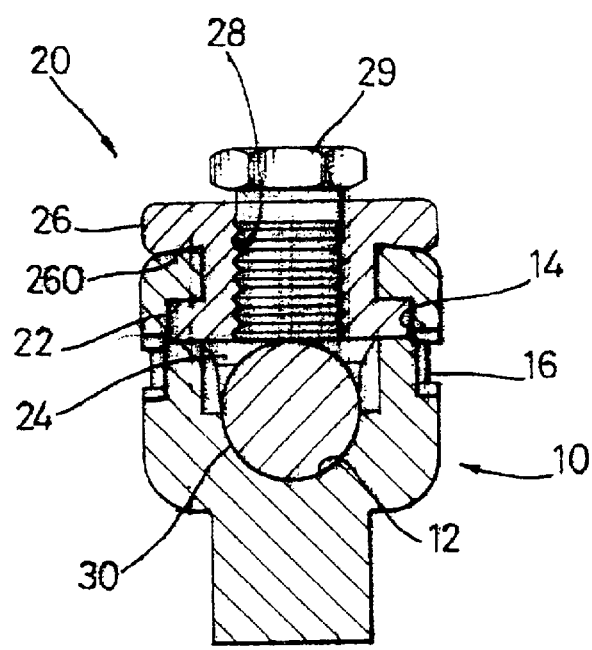
FIG. 4 shows a sectional view of present invention as shown in FIG. 3.

As shown in FIGS. 1–4, a backbone fixing device of the present invention comprises a fixation seat 10, a fixation block 20, and a fastening bolt 29.

The fixation seat 10 is provided with a U-shaped receiving slot 12 which has two retaining recesses 14 on the two inner walls, and two clamping slots 16 on the outer walls.

The fixation block 20 has a cylindrical body, and is provided with a rotary control end 26 at one end of the cylindrical body, a threaded through hole 28 at the axial center of the cylindrical body, two opposite retaining edges 22 protruding radically from the cylindrical body at the other end thereof, and an arcuate surface 24 on the other end of the cylindrical body. The arcuate surface 24 is further provided with two opposite protruded edges 240.

A fixation rod 30 is fastened by the device of the present invention such that the fixation rod 30 is received in the receiving slot 12 of the fixation seat 10, and that the fixation rod 30 is pressed against by the fastening bolt 29 which is engaged with the threaded through hole 28 of the fixation block 20. The retaining edge 22 of the fixation block 20 is retained in the retaining recesses 14 on the inner walls of the receiving slot 12 of the fixation seat 10.

The fixation rod 30 is first received in the receiving slot 12 of the fixation seat 10, and the fixation block 20 is jointed with the fixation seat 10 with the two retaining edges 22 being aligned with the fixation rod 30, wherein the fixation rod 30 is held by the arcuate surface 24 of the fixation block 20 with the two protruded edges 240 contacting the fixation rod 30 laterally. As the rotary control end 26 of the fixation block 20 is turned, the two retaining edges 22 will be retained in the two retaining recesses 14 on the inner walls of the receiving slot 12 of the fixation seat 10, and the two protruded edges 240 will be shifted to two different points without crossing the fixation rod 30, so that the fixation rod 30 is temporarily held by the arcuate surface 24 of the fixation block 20. The fixation rod 30 is held securely in the fixation seat 10, when it is pressed against by the fastening bolt 29 which is engaged with the threaded through hole 28 of the fixation block 20.

Figure 5:
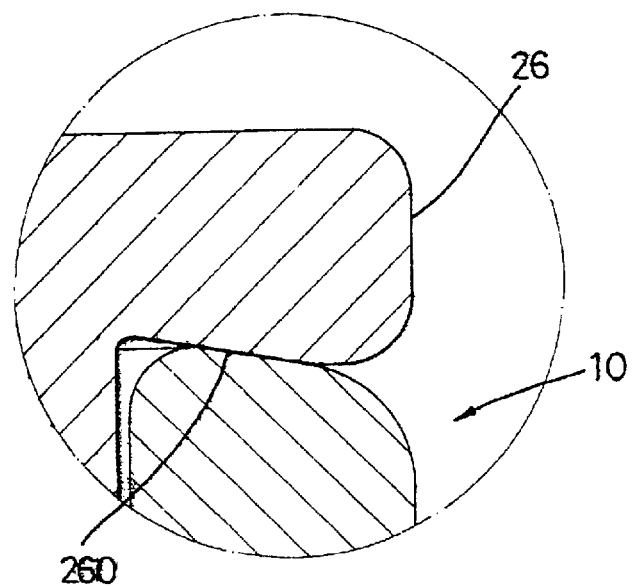
FIG. 5 shows a partial enlarged view of the present invention as shown in FIG. 4.

As illustrated in FIG. 5, the inclined surfaces of the underside 260 of the rotary control end 26 of the fixation block 20 and the top edge of the side walls of the fixation seat 10 come in contact with each other to produce an inward push, which gives the fixation seat 10 an added strength to hold securely the fixation block 20 and the fixation rod 30.

Figure 6:
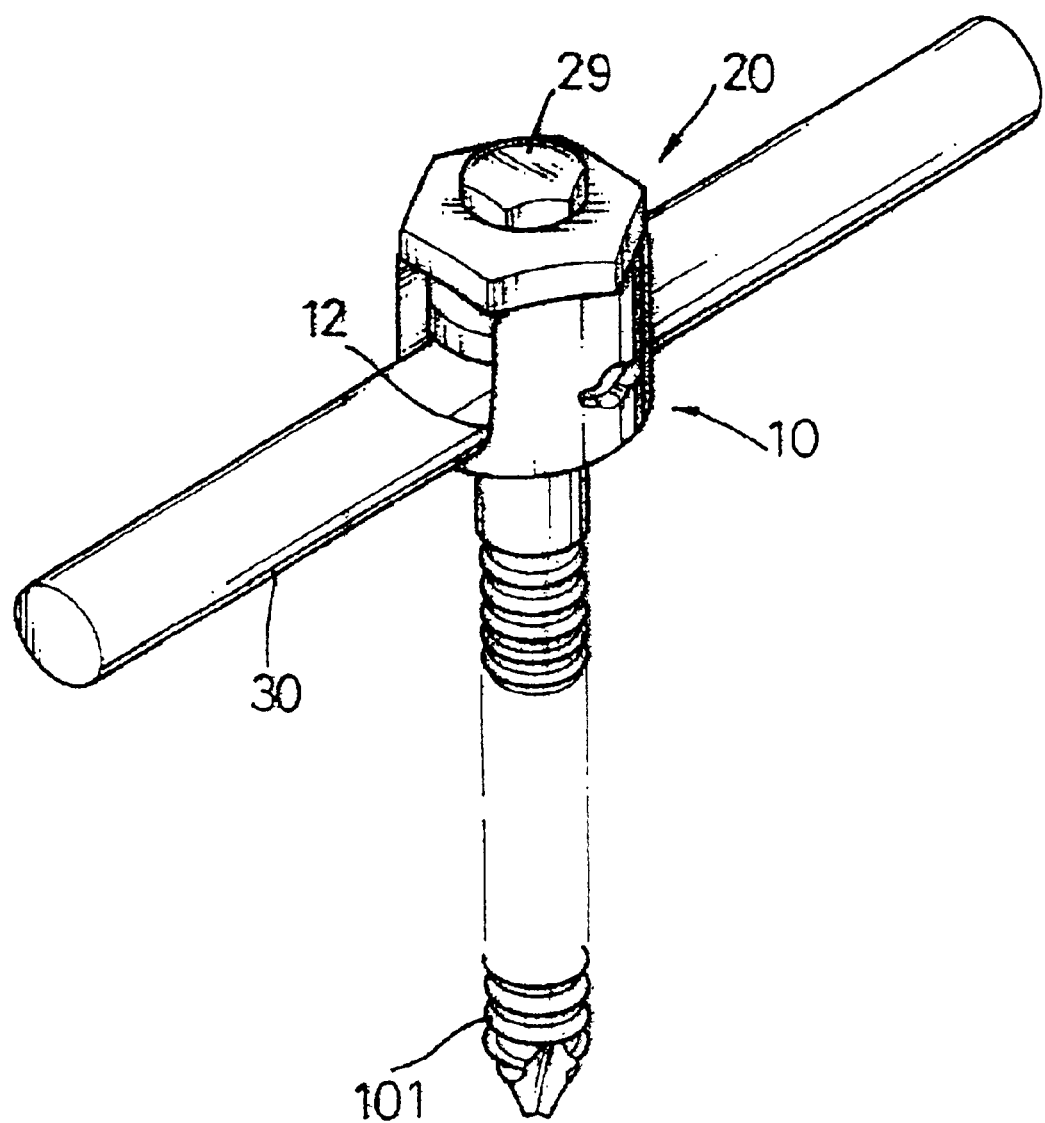
FIG. 6 shows a perspective view of the present invention in conjunction with a screw.
Figure 7:
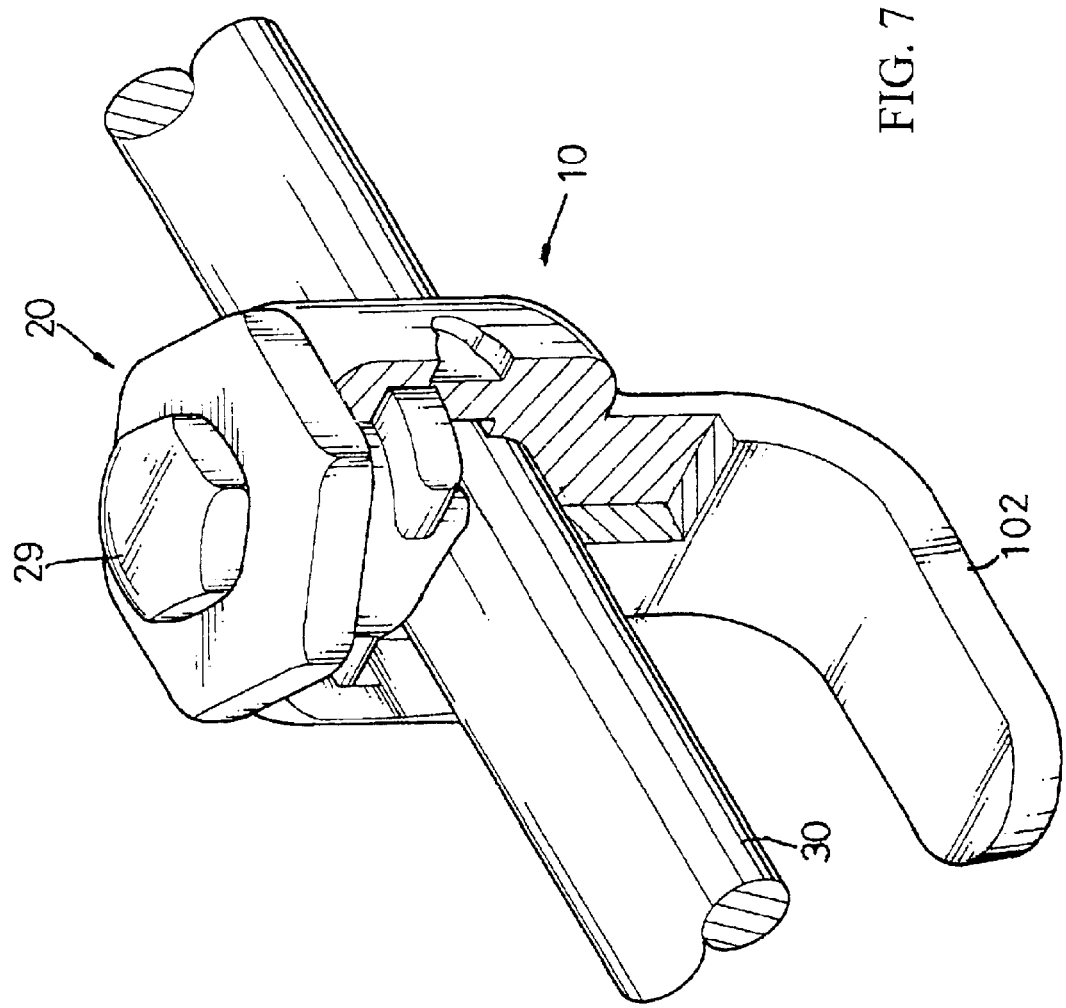
FIG. 7 shows a perspective view of the present invention in conjunction with a hooked body.

As shown in FIG. 6, the fixation seat 10 is provided with a fastening screw 101 which is made integrally therewith for fastening onto a bone. The fastening screw 101 may be replaced by a hooked body 102 for catching a spinal segment under treatment, as shown in FIG. 7.

Figure 8:
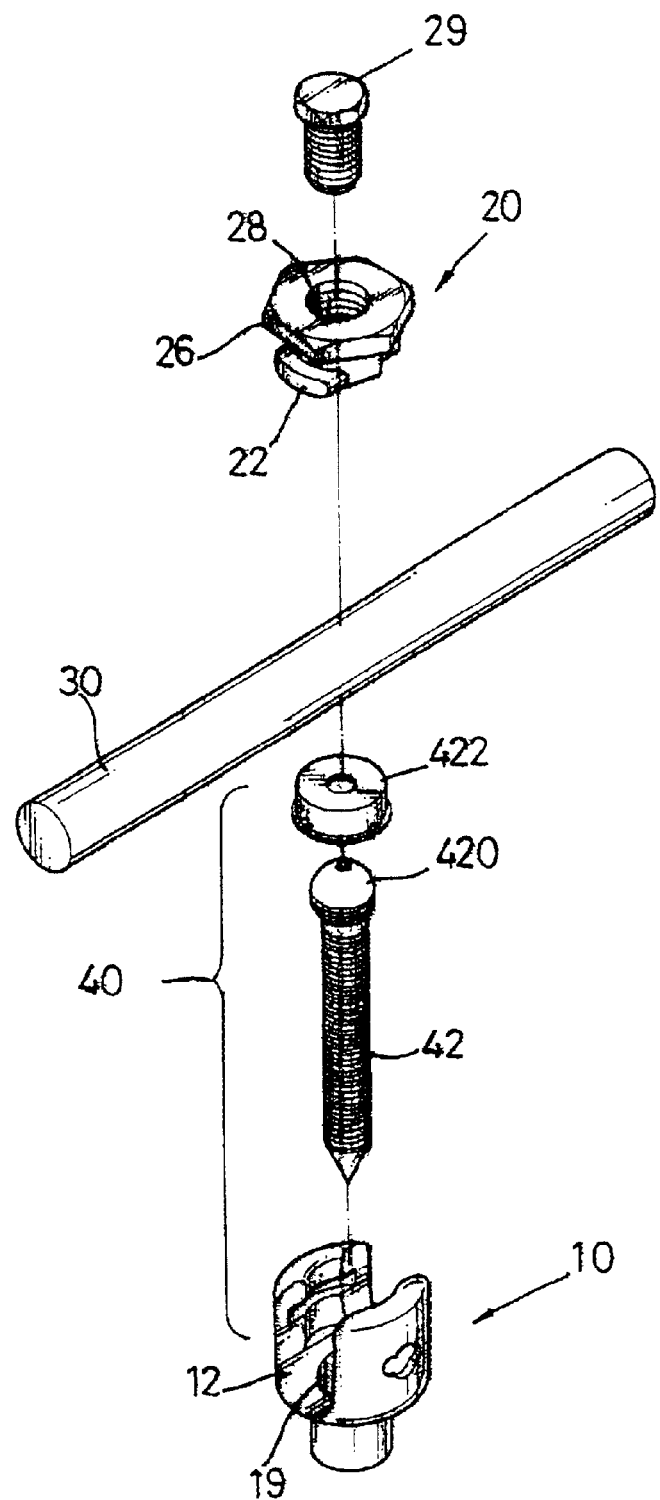
FIG. 8 shows an exploded view of a second preferred embodiment of the present invention.
Figure 9:
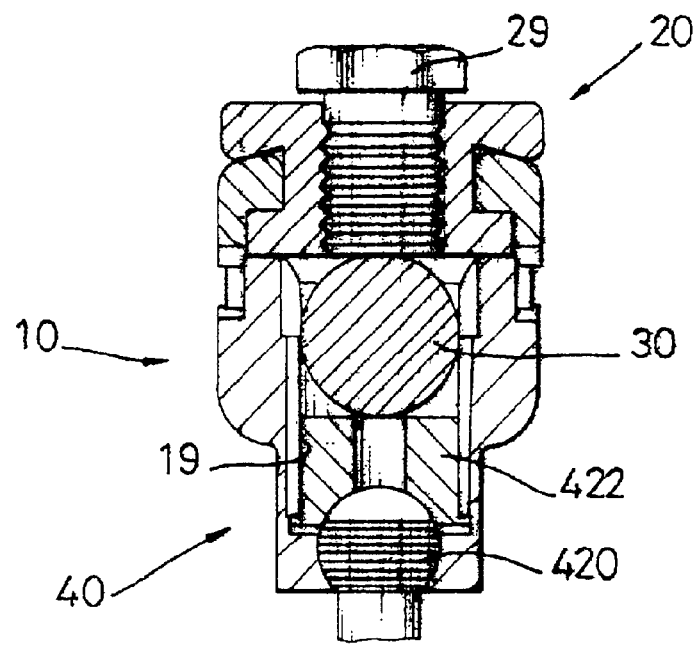
FIG. 9 shows a sectional view of the second preferred embodiment of the present invention in combination.

As shown in FIGS. 8 and 9, the second preferred embodiment of the present invention is basically similar in construction to the first preferred embodiment described above, except that the former comprises a spherical head fixation apparatus 40 comprising a fixation screw 42 having a spherical head 420 and a shank, and a press ring 422. The shank of the fixation screw 42 is put through the through hole 19 of the fixation seat 10 such that the shank is fastened onto a spinal segment under treatment, and that the head 420 is held by the edge of the through hole 19 to prevent the escape of the fixation screw 42. The press ring 422 is rested on the spherical head 420 to secure the spherical head 420, and is pressed by the fixation rod 30. The fixation rod 30 is then fastened by the fixation block 20.

Figure 10:
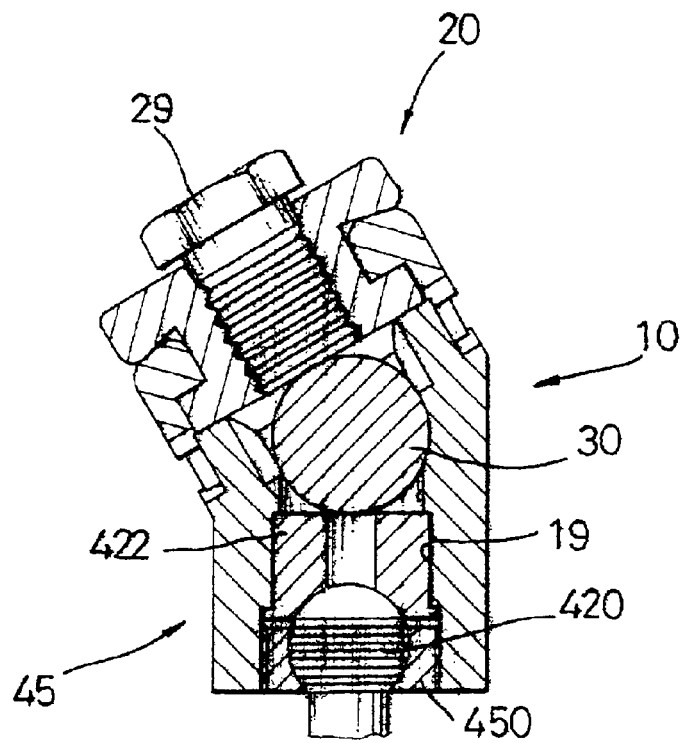
FIG. 10 shows an sectional view of a third preferred embodiment of the present invention in combination.

As shown in FIG. 10, a second spherical head fixation apparatus 45 is used in conjunction with the fixation seat 10 and an assembly ring 450. The head 420 is joined with the assembly ring 450 before the fixation screw 42(shown in FIG. 8) is fastening onto a bone. The press seat 422 is joined with the assembly ring 450, thereby enclosing the head 420. The press seat 422 and the assembly ring 450 together the head 420 are received in the through hole 19 of the fixation seat 10. In order to fixedly connect the assembly ring 450 to the fixation seat 10, threads may be formed on the inner wall of the through hole 19 and on the outside surface of the assembly ring 450. Alternatively, threaded through holes perpendicular to the through hole 19 may be provided on the fixation seat 10 and fastening bolts engageable with the threaded through holes may be provided to fixedly connect the assembly ring 450 to the fixation seat 10.

Figure 11:
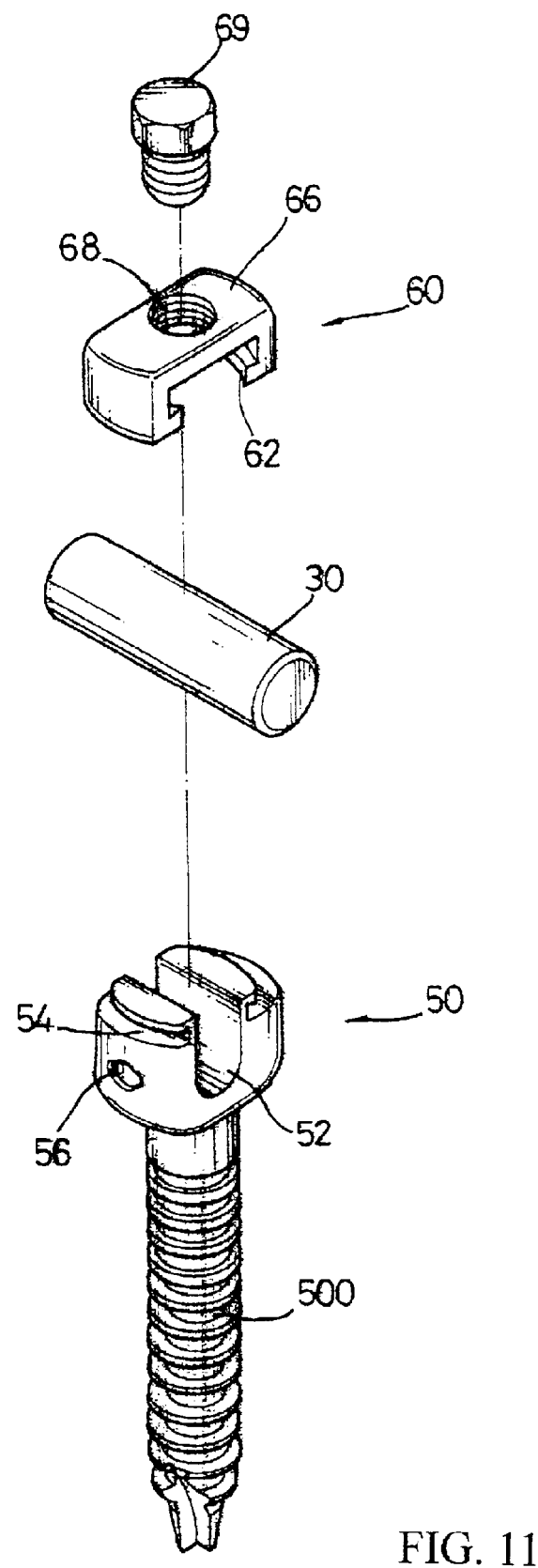
FIG. 11 shows an exploded view of a fourth preferred embodiment of the present invention.
Figure 12:
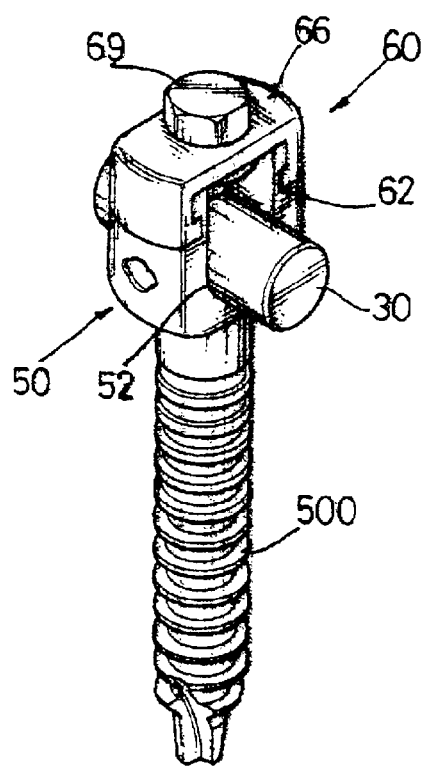
FIG. 12 shows a perspective view of the fourth preferred embodiment of the present invention in combination.
Figure 13:
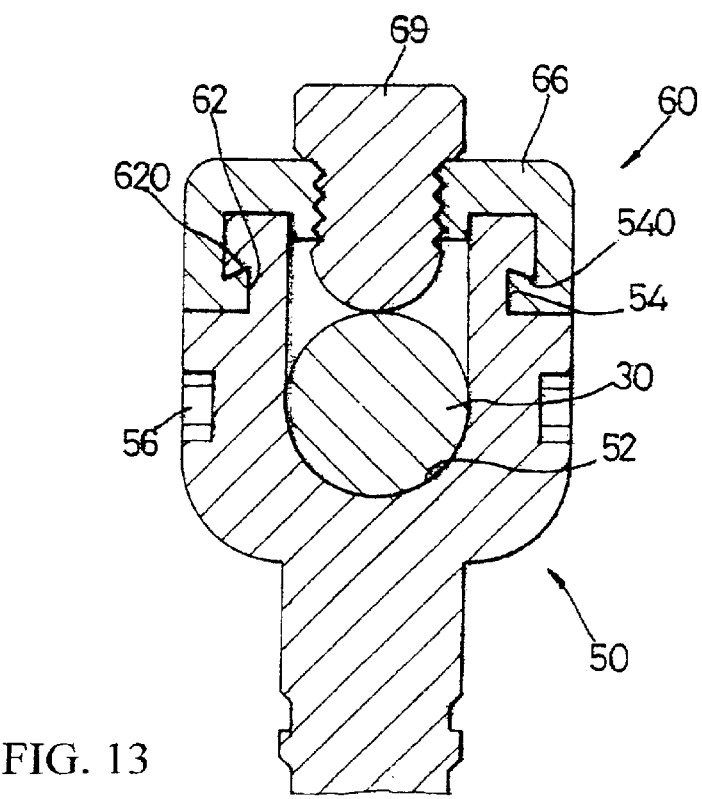
FIG. 13 shows a sectional view of the fourth preferred embodiment of the present invention as shown in FIG. 12.

As shown in FIGS. 11–13, the fourth preferred embodiment of the present invention comprises a fixation seat 50 and a fixation block 60. The fixation seat 50 is provided with a U-shaped slot 52, a tool slot 56, and a screw portion 500 or a hooked portion. The fixation seat 50 is provided on two side walls of the U-shaped slot 52 with a retaining recess 54. The fixation block 60 is provided with two retaining edges 62, which join with the retaining recesses 54 of the fixation seat 50 to form a swallow-tail shape. The retaining recesses 54 of the fixation seat 50 are located on the outer sides of the two side walls of the slot 52. The retaining edges 62 of the fixation block 60 are located on the inner sides of the fixation block 60. A fastening bolt 69 is put through a threaded through hole 68 of the control end 66 of the fixation block 60 to press against the fixation rod 30.

What is claimed is:

1. A vertebral fixation device for fastening a fixation rod which is used to fix a spinal segment under treatment, said device comprising:

a fixation seat provided with a receiving slot for receiving the fixation rod, said receiving slot having two opposite side walls, each of said side walls including a retaining recess;

a fixation block provided at a top end with a rotary control end, a threaded through hole, and two retaining edges opposite to each other, wherein said fixation block is engaged with said fixation seat such that the fixation rod is pressed against by said fixation block, and the two retaining edges are retained in said retaining recesses of said fixation seat;

a fastening bolt engaged with said threaded through hole of said fixation block such that one end of said fastening bolt presses against the fixation rod;

said retaining recesses of said fixation seat are located in inner sides of the two side walls of said receiving slot; said retaining edges of said fixation block are located in outer edges of said fixation block; and said rotary control end of said fixation block is provided in a bottom edge with an inclined plane having a higher inner side and a lower outer side; said fixation seat is provided in a top edge of the side walls thereof with an inclined plane having a higher inner side and a lower outer side; said fixation seat is engaged with said fixation block such that said inclined planes of said fixation block and said fixation seat are in contact with each other.

2. The device as defined in claim 1, wherein said fixation block is provided in an underside with an arcuate surface which is provided with a plurality of protruded edges, wherein said fixation block presses against the fixation rod in such a manner that the fixation rod is held by said protruded edges of said arcuate surface of the underside of said fixation block.

3. The device as defined in claim 1, wherein said retaining recesses of said fixation seat are located in outer sides of the two side walls of said receiving slot; wherein said retaining edges of said fixation block are located in inner edges of said fixation block.

4. The device as defined in claim 1, wherein said retaining edges of said fixation block are slanted so that the fixation rod is pressed by the fixation block at such time when said retaining edges are retained in said retaining recesses of said fixation seat.

5. The device as defined in claim 1, wherein said fixation seat is provided in outer sides of said two side walls with a clamping slot engageable with a hand tool.

6. The device as defined in claim 1, wherein said fixation seat is provided with a fastening screw made integrally therewith.

7. The device as defined in claim 1, wherein said fixation seat is provided with a hooked body made integrally therewith.

8. The device as defined in claim 1, wherein said fixation seat is provided in a bottom with a through hole, and is further provided with a fixation apparatus comprises a spherical head and a press ring, wherein said spherical head and said press ring are adapted to be received in said through hole with said press ring resting on said spherical head, and said spherical head and said press ring will be pressed securely in the fixation seat by the fixation rod, when the fixation block is joined with said fixation seat.

9. The device as defined in claim 8, wherein said spherical head is provided with a fastening screw made integrally therewith for fastening onto a bone or spinal segment, wherein said fastening screw is extruding from said through hole when said spherical head is received in said through hole.

10. The device as defined in claim 1, wherein said fixation seat is provided in a bottom with a through hole, and is further provided with a fixation apparatus comprises a spherical head, a press ring, and an assembly ring, wherein said spherical head and said press ring are adapted to be received in said through hole with said press ring resting on said spherical head, and said assembly ring which is adapted to mounted to said through hole so that said spherical head is clamped between said assembly ring and said press ring, wherein said spherical head and said press ring will be pressed against said assembly ring by the fixation rod, when the fixation block is joined with said fixation seat.

11. The device as defined in claim 10, wherein said spherical head is provided with a fastening screw made integrally therewith for fastening onto a bone or spinal segment, wherein said fastening screw is extruding from said through hole when said spherical head is received in said through hole.

* * * * *